(12) United States Patent
Ducrée (10) Patent No.: US 8,482,734 B2
(45) Date of Patent: Jul. 9, 2013

(54) CENTRIFUGAL DEVICE

(75) Inventor: Jens Ducrée, Ashbourne (IE)

(73) Assignee: Dublin City University, Dublin (IE)

( * ) Notice: Subject to any disclaimer, the term of this patent is extended or adjusted under 35 U.S.C. 154(b) by 369 days.

(21) Appl. No.: 12/667,211

(22) PCT Filed: Jun. 30, 2008

(86) PCT No.: PCT/EP2008/058390
§ 371 (c)(1),
(2), (4) Date: May 28, 2010

(87) PCT Pub. No.: WO2009/003985
PCT Pub. Date: Jan. 8, 2009

(65) Prior Publication Data
US 2010/0245815 A1  Sep. 30, 2010

(30) Foreign Application Priority Data
Jun. 29, 2007 (DE) .......................... 10 2007 030 347

(51) Int. Cl.
*G01N 21/00* (2006.01)
(52) U.S. Cl.
USPC ........... 356/436; 356/440; 356/317; 436/172; 422/68.1
(58) Field of Classification Search
USPC ..... 356/432–440, 317, 416; 436/172; 422/52, 422/68.1
See application file for complete search history.

(56) References Cited

U.S. PATENT DOCUMENTS

| 5,637,421 A | 6/1997 | Poehler et al. ................ 429/190 |
| 2001/0048895 A1 | 12/2001 | Virtanen ...................... 422/68.1 |
| 2004/0142494 A1 | 7/2004 | Sheppard, Jr. et al. ....... 436/518 |
| 2005/0179901 A1* | 8/2005 | Ostlin et al. .................. 356/445 |
| 2006/0076346 A1 | 4/2006 | Bedingham et al. .......... 219/725 |
| 2008/0277606 A1* | 11/2008 | Wang et al. ................... 250/581 |
| 2009/0035847 A1* | 2/2009 | Cho et al. .................. 435/289.1 |
| 2010/0309487 A1* | 12/2010 | Hyoudou et al. ............. 356/620 |

FOREIGN PATENT DOCUMENTS

| EP | 1672356 | | 6/2006 |
| GB | 2369428 | | 5/2002 |
| GB | 2369428 A | * | 5/2002 |
| WO | 01/38857 | | 5/2001 |
| WO | 2007/054710 | | 5/2007 |

OTHER PUBLICATIONS

Anderson, "Analytical Techniques for Cell Fractions : XIV. Use of Drainage Syphons in a Fast-Analyzer Cuvet-Rotor," *Analytical Biochemistry* 32:59-69, 1969.
Anderson, "Computer Interfaced Fast Analyzers," *Science* 166(3903):317-324, Oct. 17, 1969.

(Continued)

*Primary Examiner* — Hoa Pham
(74) *Attorney, Agent, or Firm* — Seed IP Law Group PLLC (57) ABSTRACT

A device consisting of a rotatable substrate (10) with at least one cavity (14) or channel/chamber structures is described. Fluids may be provided into the at least one cavity (14) and on rotation of the substrate will experience the effects of pseudo forces. At least one functional element (15, 16) which is based on organic conductors as for instance an LED or a photodiode is connected with the rotatable substrate.

39 Claims, 4 Drawing Sheets

OTHER PUBLICATIONS

Boettcher, M. et al., "Lab-on-Chip-Based Cell Separation by Combining Dielectrophoresis and Centrifugation," *Biophysical Reviews and Letters* 1(4):443-451, 2006.

Bundgaard, F. et al., "A Simple Opto-Fluidic Switch Detecting Liquid Filling in Polymer-Based Microfluidic Systems," *Transducers & Eurosensors '07, The 14th International Conference on Solid-State Sensors, Actuators and Microsystems*, Lyon, France, Jun. 10-14, 2007, pp. 759-762.

Dimitrakopoulos, C.D. et al., "Organic Thin-Film Transistors: A Review of Recent Advances," *IBM J. Res. & Dev.* 45(1):11-27, Jan. 1, 2001.

Ducrée, J. et al. (eds.), *FlowMap—Microfluidics Roadmap for the Life Sciences*, Books on Demand GmbH, Norderstedt, Germany, 2004, 197 pages.

Grumann, M. et al., "Batch-Mode Mixing on Centrifugal Microfluidic Platforms," *Lab Chip* 5:560-565, 2005.

Grumann, M. et al., "Visualization of Flow Patterning in High-Speed Centrifugal Microfluidics," *Review of Scientific Instruments* 76(025101):1-6, 2005.

Grumann, M. et al., "Sensitivity Enhancement for Colorimetric Glucose Assays on Whole Blood by On-Chip Beam-Guidance," *Biomed Microdevices* 8:209-214, 2006.

Gustafsson, M. et al., "Integrated Sample Preparation and MALDI Mass Spectrometry on a Microfluidic Compact Disk," *Anal. Chem.* 76(2):345-350, Jan. 15, 2004.

Haeberle, S. et al., "Centrifugo-Magnetic Pump for Gas-to-Liquid Sampling," *Sensors and Actuators A* 135:28-33, 2007.

Hua, F. et al., "Ultrathin Cantilevers Based on Polymer-Ceramic Nanocomposite Assembled through Layer-by-Layer Adsorption," *Nano Letters* 4(5):823-825, 2004.

Huang, J. et al., "Patterning of Organic Devices by Interlayer Lithography," *J. Mater. Chem.* 17:1043-1049, 2007.

Inganäs, M. et al., "Integrated Microfluidic Compact Disc Device with Potential Use in Both Centralized and Point-of-Care Laboratory Settings," *Clinical Chemistry* 51(10):1985-1987, 2005.

International Search Report, mailed May 11, 2008, for PCT/EP2008/058390, 5 pages.

Lee, K.S. et al., "Direct Patterning of Conductive Water-Soluble Polyaniline for Thin-Film Organic Electronics," *Applied Physics Letters* 86(074102):1-3, 2005.

Levi, "New Printing Technologies Raise Hopes for Cheap Plastic Electronics," *Physics Today*, pp. 20-22, Feb. 2001.

Lin, C. et al., "Rotation Rate Measurement of a Microfluidic Biodisk Spinner and Automatic Adjustment for the Pulsed Light Source," *Optics & Laser Technology* 39:202-209, 2007.

Madou, M.J. et al., "The LabCD™: A Centrifuge-Based Microfluidic Platform for Diagnostics," *Proceedings of SPIE—Systems and Technologies for Clinical Diagnostics & Drug Discovery* 3259:80-93, 1998.

Madou, M. et al., "Lab on a CD," *Annu. Rev. Biomed. Eng.* 8:601-628, 2006.

Pardo, D.A. et al., "Application of Screen Printing in the Fabrication of Organic Light-Emitting Devices," *Advanced Materials* 12(17):1249-1252, Sep. 1, 2000.

Parthasarathy, G. et al., "A Full-Color Transparent Metal-Free Stacked Organic Light Emitting Device with Simplified Pixel Biasing," *Advanced Materials* 11(11):907-910, 1999.

Pugia, M.J. et al., "Microfluidic Tool Box as Technology Platform for Hand-Held Diagnostics," *Clinical Chemistry* 51(10):1923-1932, 2005.

Riegger, L. et al., "Single-Step Centrifugal Hematocrit Determination on a 10-$ Processing Device," *Biomed Microdevices* 9:795-799, 2007.

Riegger, L. et al., "Automated Hematocrit Measurement and Patient Data Labeling by a Commercial DVD-Writer with a Low-Cost Optical Add-On," *Eleventh International Conference on Miniaturized Systems for Chemistry and Life Sciences*, Paris, France, Oct. 7-11, 2007, pp. 1249-1251.

Rogers, J.A. et al., "Nonphotolithographic Fabrication of Organic Transistors with Micron Feature Sizes," *Applied Physics Letters* 72(21):2716-2718, May 25, 1998.

Schembri, C.T. et al., "Portable Simultaneous Multiple Analyte Whole-Blood Analyzer for Point-of-Care Testing," *Clin. Chem.* 38(9):1665-1670, 1992.

Schembri, C.T. et al., "Centrifugation and Capillarity Integrated into a Multiple Analyte Whole Blood Analyser," *Journal of Automatic Chemistry* 17(3):99-104, May-Jun. 1995.

Shinar, "Monolithic Organic Light Emitting Devices (OLEDs)/Optical Chemical Sensors and Sensor Arrays," URL=www.cmp.ameslab.gov/highlights/shinar.html, retrieved Feb. 6, 2002, 1 page.

Sirringhaus, H. et al., "High-Resolution Inkjet Printing of All-Polymer Transistor Circuits," *Science* 290:2123-2126, Dec. 15, 2000.

Someya, T. et al., "Conformable, Flexible, Large-Area Networks of Pressure and Thermal Sensors with Organic Transistor Active Matrixes," *PNAS* 102(35):12321-12325, Aug. 30, 2005.

Steigert, J. et al., "Integrated Sample Preparation, Reaction, and Detection on a High-Frequency Centrifugal Microfluidic Platform," *JALA Technology Review* 10:331-341, Oct. 2005.

Written Opinion, mailed May 11, 2008, for PCT/EP2008/058390, 6 pages.

Yu, G. et al., "Dual-Function Semiconducting Polymer Devices: Light-Emitting and Photodetecting Diodes," *Appl. Phys. Lett.* 64(12):1540-1542, Mar. 21, 1994.

Yu, G. et al., "Polymer Photovoltaic Cells: Enhanced Efficiencies via a Network of Internal Donor-Acceptor Heterojunctions," *Science* 270:1789-1791, Dec. 15, 1995.

\* cited by examiner

CENTRIFUGAL DEVICE

FIELD OF THE INVENTION

The present invention refers to devices having rotatable substrates with cavities such as chambers or connection channels into which fluids may be provided. The invention more particularly relates to such devices having associated therewith functional elements, preferably fabricated from organic semiconductors. In a preferred arrangement the invention relates to a centrifugal-fluidic device having an associated organic semiconductor based functional element associated therewith, the device being configured such that during rotation of the device the fluid and the functional element are maintained in the same reference frame. Within the present disclosure the term fluid is used to describe both liquids and gases. The term fluid is also intended to encompass mixtures formed from one or more components in either liquid, gaseous or solid phases of the same or different constituents.

BACKGROUND

Centrifugal fluid devices or centrifuges are well known. Since the late 1960's centrifugal-fluidic systems have been developed and used for integrated and automated processing, in particular for analytic and diagnostic applications [Norman G. Anderson. Computer interfaced fast analyzers. Science, 166 (3903): 317-324, 1969; Norman G. Anderson. Analytical techniques for cell fractions. XIV. Use of drainage syphons in a fast-analyzer cuvette-rotor. Analytical Biochemistry, 32 (1): 59-69, 1969.]. Applications of such devices include the separation of substances. In a reference frame spinning with the rotor, the centrifugal force points away from the centre of rotation. If multiple phases are present in a channel, the laws of buoyancy teach that the denser phases settle towards the radially outer part of their container, thus displacing the less dense phases to the radially inwards part. This promotes the movement of low-density constituents towards the axis of rotation. More dense constituents of the fluids are forced to move radially outwardly under the influence of the centrifugal force.

The centrifugal field also induces a radially oriented hydrostatic pressure gradient in fluid-filled channels, containers or chambers. Fluid volumes subjected to a centrifugal field therefore tend to flow in the planes oriented perpendicular to the axis of rotation.

Such development has led to systems providing a microfluidic lab on a chip and/or μTAS (Micro Total Analysis System) and technologies developed since the beginning of the 1990's relate to centrifugal based "Lab on a disk" systems. [C. T. Schembri, Vth Ostoich, P. J. Lingane, T. L. Burd, and S. N. Courts. Portable simultaneous multiple analyte whole blood analyzer for point of care testing. Clinical Chemistry, 38 (9): 1665-1670, 1992; C. T. Schembri, T. L. Burd, A. R. Kopf-Sill, L. R. Shea, and B. Braynin. Centrifugation and capillarity integrated into a multiple analyte whole blood analyzer. Journal of Automated Methods & Management in Chemistry, 17 (3): 99-104, 1995; M. J. Madou and G. J. Kellogg. LabCD: A centrifuge based microfluidic platform for diagnostics. In G. E. Cohn and A. Katzir, editor, Proceedings of SPIE—System & Technologies for Clinical Diagnostics & Drug Discovery, volume 3259, pages 80-93, 1998.].

These devices are well known as analysis tools. In a first application the centrifuge is used to process, e.g. separate the fluid in accordance with the density of the constituents of the fluid. The analysis methodology will include a first step of exposing the fluid to a centrifugal force and then, once separation has been achieved, analyzing the sample, i.e. the rotation and the analysis are taken in two separate sequential steps. In a second arrangement, an external sensor is used to analyse the fluid during its rotation. However, as the sensor is not in the same frame of reference, i.e. it is provided in an inertial (lab) frame as opposed to the (rotating) reference frame, it is not possible to continuously interact with the fluid during the rotation of the fluid on the centrifugal device. In such a scenario there is a difficulty of discontinuous sampling at a finite frequency, i.e. with a single stationary detector the sampling occurs at most once per rotation of the fluid. A further difficulty arises in that the sensor is physically separate from the centrifuge. In the known arrangements, this physical separation is required to allow for rotation of the centrifuge as physical contact between the external sensor and the substrate within which the fluid container is defined would restrict the movement of the substrate. Apart from the discontinuous nature of the interaction of a fluid in a rotating chamber with a stationary component, the communication, e.g. of optical signals, through a gap commonly has a negative effect, e.g. regarding signal strength, background noise and overall quality.

There is therefore a need for an improved centrifugal based device.

SUMMARY

These and other problems are addressed by a device in accordance with the teachings of the present invention. Such a device provides for the association of a functional element with the substrate within which the fluid container is defined, the functional element and container being provided in the same frame of reference such that rotation of the container is accompanied by corresponding rotation of the functional element at the same rotational frequency, i.e. a fixed spatial arrangement between them at all times. The functional element is desirably fabricated from an organic semiconductor material. Such materials are vapour-phase or solution processable and can optionally be integrated onto the substrate as part of the fabrication process for the device. The functional element may be provided in a variety of forms depending on the specifics of the application required. For example, the functional element could be fabricated in the form of a detector and using such a device it is possible to enable a continuous, 360°, observation of the fluid sample during rotation. Furthermore, as the detector is intimately coupled to the substrate, there is a direct contact of the detector with the substrate which can improve the efficiency of signal recording.

DETAILED DESCRIPTION OF THE DRAWINGS

The teaching of the present invention will now be described with reference to exemplary arrangements thereof which will be described with reference to FIGS. 1 to 4. It will be understood by those skilled in the art that the specifics of these exemplary arrangements are provided to assist in an under-standing of the teaching of the invention and it is not intended to limit the teaching to that described.

Figure 1:
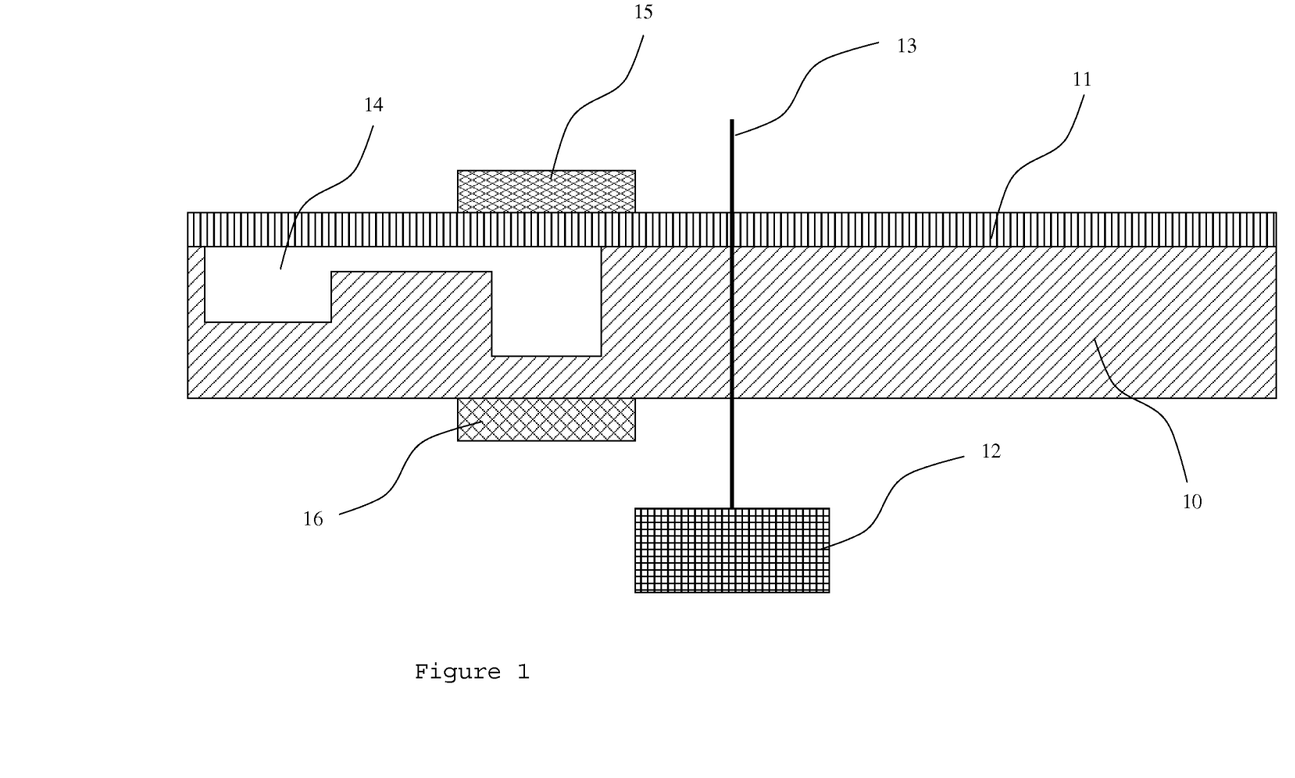
FIG. 1 is a section through a device provided in accordance with the teaching of the invention.

As shown in FIG. 1, a device provided in accordance with the teaching of the present invention includes a rotatable substrate (10) with a lid (11), such as will be appreciated by those skilled in the art. The substrate (10) is coupled to or mounted on a rotary drive (12) and through action of the rotary drive is rotatable about an axis of rotation (13), which is desirably substantially perpendicular to the major plane of the substrate. The rotatable substrate (10) provides or has defined therein one or more cavities (14) which are dimensioned and arranged for the admission or receipt of fluids. These channels are formed in upper surface of the substrate and their sides and bottom are defined by the surfaces of the substrate, the top of the cavity being defined by the lid (11). The fluids could be provided into the cavity (14) at the time of manufacture of the substrate or will be provided into the cavity at the time of use of the device. In this way, the cavity defines a sample collection volume wherein the sample may be provided at the time of sampling.

It is not intended to limit the teaching of the present invention to any one specific method of sample introduction. In this exemplary arrangement, the sample includes a first (15) and second (16) functional element which are provided on opposite sides of the substrate and separated from one another by the cavity (14). In FIG. 1, the first functional element provides a radiation source (15) and the second provides a photodetector (16). At least one of these elements is fabricated at least partially from an organic semiconductor material. In use electromagnetic radiation, typically light, will be emitted from the radiation source into the fluid sample within the cavity (14) and the resultant signal will be collected by the detector on the opposite side of the cavity (14). The nature of the collection will depend on the nature of the sample and the incident radiation. For example the sample detector (16) could provide a simple absorption response characteristic of the fluid sample or could be configured to detect a luminescent based signal output generated by the fluid sample in response to photo-excitation from the radiation source.

Figure 2:
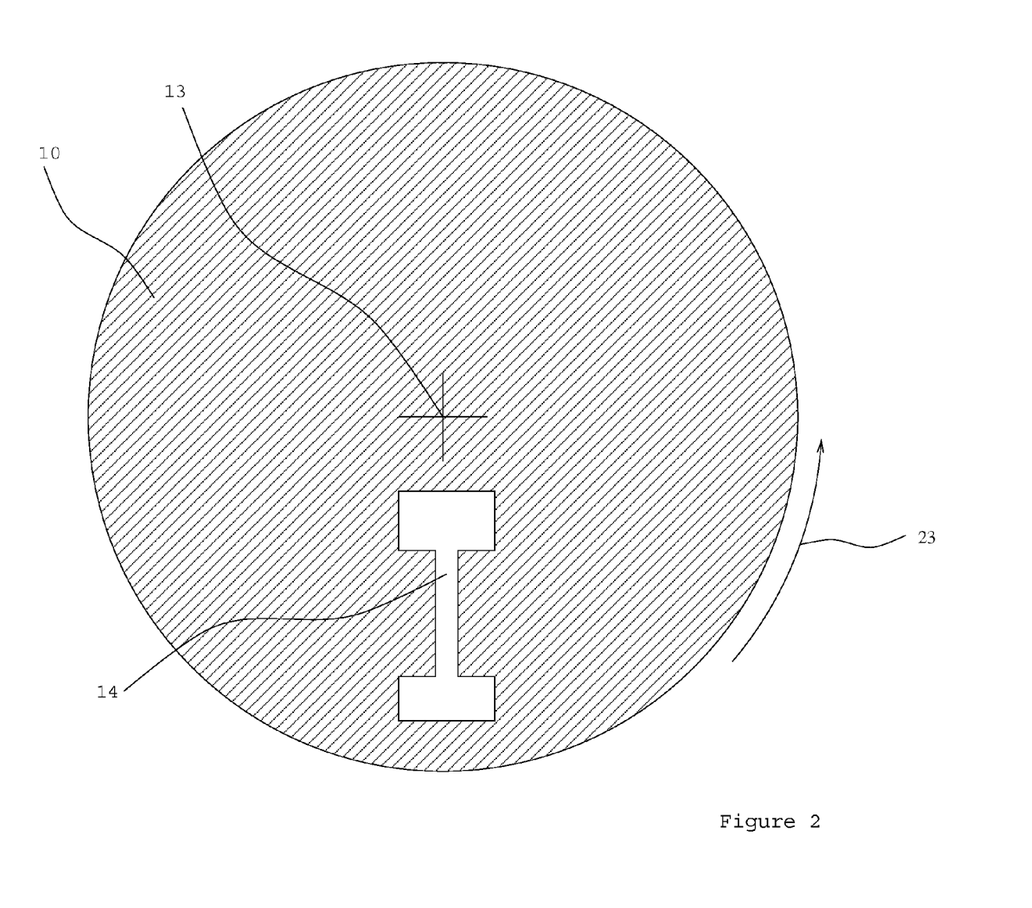
FIG. 2 is a top view of the device of FIG. 1.

As shown in FIG. 2, the cavity (14) is orientated so as to extend radially relative to the axis of rotation (13). In this way a hub and spoke configuration is defined. The structures can also be partially inclined to the radial direction in alignments well known from prior art. While only one spoke, the cavity (14), is shown in FIG. 2, it will be appreciated that a plurality of cavities could be provided in a radial fashion about the axis (13). By providing a plurality of cavities, and associating each of these with their respective individual functional element, it possible to provide a plurality of simultaneous measurements. Depending on the nature of the fluid provided in the individual cavities and/or the nature of the specific functional elements, these measurements could provide the same or different outputs.

On rotation of the substrate (10) in a defined direction and frequency of rotation (23), the individual cavities (14) will rotate around the axis of rotation (13). By providing a fluid within the chambers or cavities, a rotation of the substrate will effect a corresponding rotation of the fluid. The rotation of the substrate will result in the fluids within the chamber experiencing an applied force, the nature of the force being dependent on the nature of the rotation. Examples of the type of forces that may be experienced by the fluid within the chamber include those forces known as pseudo forces whose nature is dependent on the rotation of the reference frame. Such pseudo forces are well known in the art and include a centrifugal force resultant from a rotating reference frame with a uniform angular velocity, a Coriolis force which depends on the velocity of the fluid within the chamber and a Euler force which arises in circumstances when the angular velocity is time dependent.

By associating at least one functional element with the rotatable substrate and allowing the functional element to rotate at the same rate as that of the cavity, each of the functional element and the fluid within the cavity are maintained in the same reference frame during rotation. In the example of FIG. 1, a first and second functional element is provided, the first being configured to pass a signal into the fluid and/or induce a response within the fluid and the second being used to determine a response from the fluid. As each of these functional elements will rotate with the substrate, it is possible to continuously sample the fluid during its rotation. It will be appreciated that depending on the nature of the analysis being conducted that it is not necessary for both inducement and detection to be provided by an integrally provided functional element.

While the dimensions of the device are not evident from an inspection of FIG. 1 or 2, in a preferred exemplary arrangement the cavities provide one or more micro fluidic structures within or on the rotary substrate (10) and within which liquid quantities in the volume range of nanoliters to milliliters may be provided. Using volumes within this range it is possible to induce effects such as those relating to interfacial tension, surface tension and viscosity-governed laminar flow.

In accordance with a preferred implementation of a device provided in accordance with the teaching of the present invention, the fluid sample is exposed to effects of the induced pseudo forces resultant from the rotation of the substrate together with such forces resultant from the geometrical configuration and surface properties of the cavities such as the interfacial tension, defined capillary forces, siphon effects etc. Additional external stimuli such as heat, electromagnetic radiation or effects resultant from removable barriers such as sacrificial layers may also be provided by one or more functional elements which may optionally be provided from elements based on organic semiconductors. These functional elements may be configured to provide one or more fluid valves, switches, routers, metering structures and mixers.

It will be appreciated that the subjection of a fluid within a sample cavity to the pseudo forces resultant from controlled rotation of the substrate can serve to minimize the effects of viscosity or surface tension that often dominate results from analysis tools that incorporate stationary as opposed to rotational sampling techniques.

For example, as will be appreciated by those skilled in the art, centrifugal pumping is different than for example that achieved with piston, syringe or micro-gear pumps due to the continuous, pulse-free nature due to the mass inertia of the rotor which stabilizes the rotating motion. Fluctuations of the pressure source can lead within many applications to problems such as the distortion of liquid segments, the formation of gas bubbles by cavitation or also to the destabilization of boundary surfaces in multiphase systems. These effects are not as noticeable in a centrifuge based system.

Furthermore, due to that quasi contactless nature of the applied centrifugal force onto the contained fluid within the chambers, no pressure tight interfaces, such as tubings or connection to external pumps, are required. Furthermore, it is possible to effect a substrate change (with a corresponding change in the available sample cavities) without requiring complex connecting and loosening of pressure tight hose connectors. In this way, a device provided in accordance with the teaching of the present invention is particularly user friendly and can be used without any specific technical expertise. Furthermore, as the sample volume is integrally provided within the rotatable substrate, problems arising from coupling technologies and the maintenance that is associated therewith are minimized. Dead volumes within the sample chamber, such as those experienced in stationary sample devices, are also reduced.

The rotatable substrate (10) can be provided in any one of a number of different configurations or arrangements. Preferred formats include substantially flattened or planar disks having dimensions such as those conventionally provided in commercial Compact Discs ("CD") or also pie-segment shaped and rectangular standard microscope carriers ("Slides"). In addition, it will be appreciated that the rotational substrate could be provided in configurations such as those provided by non-planar substrates, punched structures or also rotationally symmetric substrates such as reaction tubes.

Furthermore, the rotatable substrate can be fabricated in a choice of materials or a combination of materials. Suitable exemplary materials that could be used in fabrication of such substrates include for example polymers, silicones, glass, silicon, metal, ceramic(s) or also sacrificial materials such as waxes, hydraulic gels, oils or foils as well as typical stationary phases like porous diaphragms, fleeces, frits and accumulated particles.

The substrate can also be treated or applied with global or localized coatings. For example a hydrophilic surface treatment could be applied generally across a surface of the substrate with one or more locally limited coatings such as hydrophopic localized regions for provision of for example valves or the like. These coatings can affect inter alia the interfacial tension between the fluid and the walls of the cavities and affect for example the thermal, optical or electrical isolation properties of the device.

Furthermore such surface coatings can affect the interaction with fluid components, e.g. of nucleic acids, proteins, particles or cells. On the one hand the non-specific adsorption can be suppressed or specific bonds to probe molecule may be formed to specifically capture target molecules in the fluid sample, for example in form of a bio sensor or a micro array.

The rotatable substrates and its applied coatings and functional elements can interact further with electromagnetic radiation, e.g. over wavelengths specific transmission, absorption, reflection, refraction, heat generation, waveguides or to excite evanescent fields and/or (surface) plasmons. Furthermore, one or more functional elements may be provided for activities such as recording of temperature, for pressure generation, for mechanical interaction, for tension production, for energy production, for energy transformation, for the production of surface waves, for the production of plasmons, for the production of evanescent fields, for power supply, for optical beam guidance (components such as may be provided by lenses, lattices, prisms, filters, coatings, or transverse electromagnetic waves), as well as for the transmission, processing, storage and visualization of data. It will be appreciated that the nature of the functional device provided and its interface with the rotatable substrate is limited by its ability to withstand pseudo forces generated through rotation of the substrate.

It will be appreciated that similarly to traditional or known centrifugal-microfluidic arrangements that a device provided in accordance with the teaching of the present invention can be provided as part of laboratory automation systems and can also be used for the fluid handling of more complex laboratory protocols. In this way techniques such as those described in M. Madou, J. Zoval, G. Jia, H. Kido, J. Kim and N. Kim. Lab on a CD. Annual Review of Biomedical Engineering, 8:601-628, 2006; M. Gustafsson, D. Hirschberg, C. Palmberg, H. Jörnvall, and T. Bergman. Integrated sample and MALDI mass spectrometry on a microfluidic compact disk. Analytical Chemistry, 76 (2): 345-350, 2004; Mats Inganäs, Helene Dérand, Ann Eckersten, Gunnar Ekstrand, Ann Kristin Honerud, Gerald Jesson, Gunnar Thorsén, Tobias Söderman, and Per Andersson. Integrated microfluidic compact disc devices with potential use in both centralized and point of care laboratory settings. Clinical Chemistry, 51 (10): 1985-1987, 2005; Michael J. Pugia, Gert Blankenstein, Ralf-Peter Peters, James A. Profitt, Klaus Kadel, Thomas Willms, Ronald Sommer, Hai Hang Kuo, and Lloyd S. Schulman. Micro fluidic tool box as technology platform for handheld diagnostics. Clinical Chemistry, 51 (10): 1923-1932, 2005; J., M. Grumann, T. Brenner, K. Mittenbühler, T. Nann, J. Rühe, I. Moser, S. Haeberle, L. Riegger, J. Riegler, W. Bessler, R. Zengerle, and J. Ducrée. Integrated sample preparation, reacting and detection on a high frequency centrifugal microfluidic platform. JALA—Journal of the Association for Laboratory automation, 10 (5): 331-341, 2005 can be employed with devices provided in accordance with the teaching of the present invention.

It will be further appreciated that it is not intended to limit the teaching of the present invention to devices which are self consistent, i.e. that require no interface with components outside the rotational frame of reference. In this way it will be appreciated that certain devices which incorporate elements provided in accordance with the teaching of the present invention may be capable of interacting with elements provided in the stationary frame of reference, i.e. a system may be provided including both stationary components and devices such as that heretofore described. In such arrangements it is necessary to enable communication—be that transmission of data or power coupling between the elements in the stationary frame and those in the rotating frame. To optimize such interaction, the substrate could be modified to include for example coupling structures such as V-grooves which can be provided to selectively redirect signals along or within the substrate to extend the path of the received signals with the device, so as to prolong its interaction with the fluid sample within the cavity. Such V-grooves are described in M. Grumann, J. Steigert, L. Riegger, I Moser, B. Enderle, G. Urban, R. Zengerle, and J. Ducrée. Sensitivity enhancement for colorimetric glucose assays on whole blood by on chip beam guidance. Biomedical Microdevices, 8 (3): 209-214, 2006, and could be employed within a device provided in accordance with the teaching of the present invention.

Furthermore a device provided in accordance with the teaching of the present invention could be employed to investigate boundary surfaces for example for level regulation using techniques such as those described in F. Bundgaard, O. Geschke, R. Zengerle, and J. Ducrée. A simple opto fluidic switch detecting liquid filling in polymer based micro fluidic system. In proceedings of the 14th International Conference on Solid State Sensors, Actuators & Microsystems (Transducers '07), June 10-14, Lyon, France, volume 1, pages 759-762, 2007.

Furthermore a device provided in accordance with the teaching of the present invention could employ one or more mechanical actuators which are actuated through rotation of the substrate. Such actuators could employ for example polarized stationary magnets which through rotation of the substrate could be used to induce mixing, dispersing or pumping effects. One exemplary technique for providing such pumping is described in S. Haeberle, N. Schmitt, R. Zengerle, and J. Ducrée. Centrifugo-magnetic generation of gas-liquid microflows. Sensor & Actuators A—Physical, 135 (1): 28-33, 2007. An efficient mixer is described in M. Grumann, A.

Geipel, L. Riegger, R. Zengerle, and J. Ducrée. Batch mode mixing with magnetic beads on centrifugal microfluidic platforms. Lab on A chip, 5 (5): 560-565, 2005.].

It will be appreciated that the association of the rotatable substrate with the functional elements can be achieved in any one of a number of methodologies such as for example those provided in thick-film technologies, thin-film technologies, bulk machining, stamping, printing processes or "reel-to-reel" manufacturing techniques.

If integrated into a larger system, fluids such as sample liquids or reagents can be supplied into the defined cavity of the rotatable substrate either by additional dispensers or pipettes in the peripheral system by way of appropriate inlets while the substrate is halted or also during the rotation. It is desirable that where the inlet is accessible, that the inlet is provided proximal to the axis of rotation such that during rotation of the substrate that the fluid within the chamber will be biased away from the inlet and will not leak out of the same inlet.

In addition, reagents can be pre-stored on the rotatable substrate. In such arrangements it is desirable that the pre-stored reagent would be provided in a distinct or separate chamber provided within the substrate, release of the agent being effected through provision of external stimuli such as applied electromagnetic radiation, the application of heat or induced mechanical effects. Furthermore, the device may include removable diffusion barriers or the like which are inserted to the chambers of the pre-formed liquid volumes. Such reagents could also be provided in the dry form such as lyophilized reagents.

It will be appreciated that known microfluidic systems may also be employed with stroboscopic measuring systems, which provided for the observation of fluid procedures during the rotation by means of stationary cameras or detectors. Examples of such systems include those described in M. Grumann, T. Brenner, C. Beer, R. Zengerle, and J. Ducrée. Visualization of flow patterning in high speed centrifugal microfluidics. Review of Scientific of instrument, 76 (2): 025101, 2005; Chern Sheng Lin, Chia striking Lin, Chao Ying Wu, Hong Zong Shieh and Chi Chih Lay. Rotation rate measurement of a microfluidic biodisk spinner and automatic adjustment for the pulsed light source. Optics & Laser Technologies, 39 (1): 202-209, 2007, and could equally be employed with a device provided in accordance with the teaching of the present invention.

While the specifics of the peripheral device that may be usefully employed to achieve a rotation of the rotatable substrate have not been described, it will be understood from for example L. Riegger, M. Grumann, J. Steigert, S. Lutz, C. P. Steinert, C. Mueller, J. Viertel, O. Prucker, J. Rühe, R. Zengerle, and J. Ducrée. Single step centrifugal hematocrit determination on a $10 processing device. Biomedical Microdevices, 2007. Status: on-line first (doi: 10.1007/s10544-007-9091-1); L. Riegger, J. Steigert, S. Lutz, W. Streule, R. Zengerle, and J. Ducrée. Automated hematocrit measurement and patient labelling by a commercial DVD writer with a low cost optical add-on. In Jean Louis Viovy, editor, proceedings of the 11th International Conference on Miniaturized Systems for Chemistry and Life Sciences (µTAS 2007), October 7-11, Paris, France. Chemical and Biological Microsystems Society, 2007. Status: accepted, publication in the proceedings of the conference on 7 Oct. 2007 that a peripheral device of the type having a rotary motor with electromagnetic radiation source and a detector can be provided in the form of a commercially available or only slightly modified Compact Disc/DVD player. These devices are already (in the middle of 2007) commercially available for prices less than € 20 and with maintenance costs being negligible. It will be understood that devices such as that provided in accordance with the teaching of the present invention can be implemented at prices negligible when compared to other lab-on-a-chip assemblies.

While FIGS. 1 and 2 described a device providing an integrally provided detector, a device provided in accordance with the teaching of the invention may require transfer of information to an external frame of reference. In some applications this transfer can be effected through transmission of electromagnetic (EM) radiation signals between stationary components and the rotatable substrate. Examples for this are transmitters and receivers for data signals. For example, a sensor device provided on the rotatable substrate may be coupled to a transmitter so as to enable a transfer of measured data to a receiver provided as part of a stationary control unit. In a similar fashion, control signals may be received from an external stationary controller to regulate components on the rotatable substrate device. Both the exchange of analogue and of digital signals is possible. For example radiation energy originating from a stationary radiation source can be provided contactlessly to a functional element provided as part of the rotatable substrate. If the functional element is configured in the form of, for example, a photovoltaic cell this received energy can be converted into electrical energy for the subsequent supply to other functional elements provided as part of the rotatable substrate. If the photovoltaic cell is dimensioned or provided on the substrate in the form of for example concentric circles or rings, then through temporal modulation of the radiation emitted from the stationary radiation source may be used to effect the generation of electrical signals on the substrate independent of the frequency of rotation of the substrate relative to the stationary source.

An example of such a technology is a battery-operated electrode system for the centrifugal dielectrophoresis separation of cells [M. Boettcher, M. S. Jaeger, L. Riegger, J. Ducrée, R. Zengerle, and C. Duschl. Lab on chip based cell separation by combining dielectrophoresis and centrifugation. Biophysical Reviews & Letters, 1 (4): 443-451, 2006.]. However for cost and safety reasons such multiple component hybrid systems have to date remained limited to the academic environment. Resorting to functional elements fabricated from organic semiconductors in accordance with the teaching of the invention may be used to address these severe shortcomings of prior art.

It will be appreciated that by employing functional elements fabricated from organic semiconductors that devices provided in accordance with the teaching of the invention benefit from many of the advantages associated with such devices. The use of organic semiconductors in the fabrication of any one of a number of different functional elements will be well known to those skilled in the art and within the context of the present invention it is not intended to limit the application of the teaching to any one specific class or type of element. For example it is known that organic semiconductor in arrangements with EL layers can be used as photodiodes [G. Yu, C. Zhang, A. J. Heeger. Dual function semiconducting polymer devices: Light emitting and photodetecting diodes. Applied Physics Letters, 64/12): 1540-1542, 1994], photovoltaic cells and displays. [G. Parthasarathy, G. Gu, S. R. Forrest. A full color transparency metal free stacked organic light emitting device with simplified pixels biasing. Advanced of material, 11 (11), 907-910, 1999.], photovoltaic cells [G. Yu, J. Gao, J. C. Hummelen, F. Wudl, A. J. Heeger]. Polymer photovoltaic cells: Enhanced efficiencies via a network of internal donor acceptor hetero-junctions. Science, 270 (5243): 1789-1791, 1995.], Transistors and from it developed electronic circuits [C. D. Dimitrakopoulos and D. J. Mascaro. Organic thin film of transistor: A review of recent advances. IBM journal OF Research & development, 45 (1): 11-27, 2001.], Batteries [patent specification U.S. Pat. No. 5,637,421], Cantilevers [F. Hua, T. Cui, Yuri M. Lvov. Ultra thin cantilevers based on polymer ceramic nano-composites assembled through layer by layer adsorption. Nano Letters, 4 (5): 823-825, 2004.] and sensors [T. Someya, Y. Kato, T. Sekitani, S. Iba, Y. Noguchi, Y. Murase, H. Kawaguchi, T. Sakurai. Conformable, flexible, large area network of pressure and thermal sensor with organic transistor active matrixes. Proceedings of the National Academy of Sciences of the USA, 102 (35): 12321-12325, 2005.].

Figure 3:
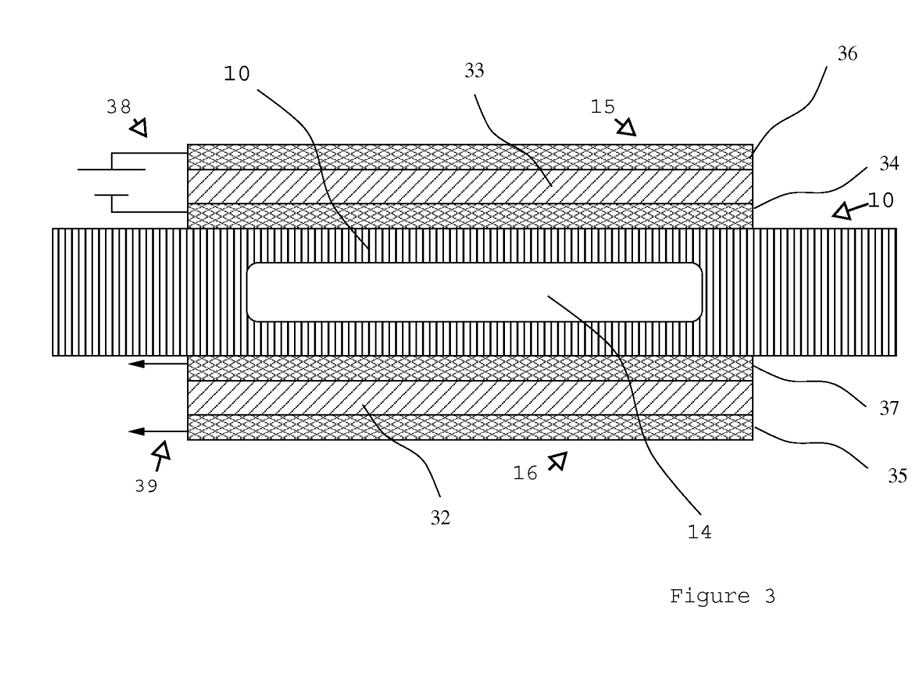
FIG. 3 is a sectional view of portion of a device provided in accordance with the teaching of the present invention.

FIG. 3 shows a detailed view of the type of arrangement that may be employed to provide the detector and sensor arrangement of FIG. 1. The same reference numerals will be used for similar components. A rotatable substrate (10) provides a cavity (14). Two functional elements 15, 16 are provided on either side of the cavity and respectively provide an LED 15 and a photodiode 16. Each of the two elements is fabricated from a multilayer structure. The LED (33; 34; 36) is fabricated from an organic EL layer (33) provided between a cathode (36) and a transparent anode (34). Radiation is emitted by the LED by application of an applied potential from a power supply (38). In a similar fashion, the photodiode is fabricated from a transparent anode (37) layered with a intermediary organic EL layer 32 and a cathode (35) and generates an output signal (39) in response to a voltage difference between the anode (37) and the cathode (35) resultant from the incident EM radiation. It will be appreciated that this simple layer structure is exemplary of the type of structure that may be fabricated from the organic semiconductor elements. Such a layered structure may be modified for different applications. For example in a fluorescence measurement system, emission and detection filters can be planned into the path of rays between radiation source and detector using for example PDMS or silicone based filters.

It will be appreciated that by providing a plurality of functional elements such as, for example, an array of LEDs and/or photodiodes that it is possible to spatially discriminate the characteristics of a fluid within a defined cavity over a detection area.

It will be appreciated that the fabrication of the functional elements may be employed using any one of a number of known techniques. For example solution or vapour processing techniques such as those described in [H. Sirringhaus, T. Kawase, R. H. Friend, T. Shimada, M. Inbasekaran, W. Wu, E. P. Woo. High resolution inkjet printing of all-polymer transistor circuits. Science, 290 (5499): 2123-2126, 2000.], screen printing [J. A. Rogers, Z. Bao, V. R. Raju. Nonphotolithographic fabrication of organic transistor with micron feature of sizes. Applied Physics Letters, 72 (21): 2716-2718, 1998; D. A. Pardo, G. E. Jabbour, N. Peyghambarian. Application of screen printing into the fabrication of organic light emitting devices. Advanced Materials, 12 (17): 1249-1252, 2000.] or stamping [B. Gross Levi. New printing technologies raise hopes for cheap plastic electronics. Physics Today, 54 (2): 20-22, 2001.] may be employed. Further possibilities include lithographic [J. Huang, R. Xia, Y. Kim, X. Wang, J. Dane, O. Hofmann, A. Mosley, A. J. de Mello, J. C. de Mello, D. D. C. Bradley. Patterning of organic devices by more interlayer lithography. Journal of Material Chemistry, 17 (11): 1043-1049, 2007.] and capillary driven principles [K. S. Lee, G. B. Blanchet, F. Gao, Y.- L. Loo. Direct patterning of conductive water soluble polyaniline for thin film organic electronics. Applied Physics Letters, 86 (7): 074102, 2005].

It is also possible within the context of the present invention to adopt a hybrid structure where preformed or fabricated functional elements are fabricated separate to the rotatable structure and are then coupled to the rotatable structure. Such coupling techniques may employ known interconnection and packaging techniques such as sticking or clamping techniques. The substrates can be mechanically in each case rigid or flexible. In another implementation using appropriate material and process compatibility, it is possible to directly process both organic and also non-organic based functional elements directly on the rotatable substrate.

In harsh physical or chemical conditions it is possible to protect the substrate from contact with non-compatible, physico-chemical conditions such as humidity or chemically aggressive materials, through provision of intermediate layers with suitable barrier characteristics in different portions of the substrate. These may be provided through different manufacturing processes.

In a preferred arrangement, the use of organic semiconductor materials for the first time on rotatable platforms, on which fluids are provided, the fluids being subjected to the affect of forces resultant from the rotation of the platform is described. It will be appreciated that the frequency of rotation of the platform will affect the nature of the forces experienced and while it is not intended to limit the application of the teaching of the present invention to any type of force, exemplary forces include centrifugal, Euler, and those resultant from the Coriolis effect.

By combining the rotatable platforms or substrates with functional elements fabricated from organic semiconductors, the advantages of hydrodynamics with the advantages of the use of the type of functional components, specified above, which are based on organic semiconductors, steered via the rotating motion, can be synergetically united. By maintaining the functional elements and the fluid within the same reference frame during rotation of the fluid, the interaction between the fluid and the functional element is not restricted to any one time or position during the rotation.

By subjecting the fluid to a controlled rotation motion, the fluid is subjected to pseudo-forces. Such an arrangement has many advantages in the manner in which the fluid is handled including for example the following:

Robust handling of fluids, which can be arranged to a large extent independent of liquid characteristics such as viscosity and surface tension.

Pulse-free actuation.

Tendency for the removal of gas bubbles by centrifugally induced buoyancy.

No pressure tight interfaces necessary, thus user friendly substrate change and low maintenance work and costs.

Simplified peripheral device, which can ideally be composed of a simple, frequency-controllable rotary motor and a data processing unit.

The advantages of the use of functional elements which are based on organic semiconductors can be summarized as follows:

Integration of efficient and if necessary also large-area functional elements such as LEDs, OLEDs displays, photodiodes, photovoltaic elements and electronics to manufacturing costs, which permit the design of the substrates contrary to the realization by conventional semiconductor components as one-way, disposable solutions.

By use of the integrated system as a one-use device, the necessity for a fluid cleaning is avoided and also the problem of the potentially hazardous manual disposal of the sample material is minimized. On the other hand the problem the comparatively small life time (at shelf or on duty) of functional elements on basis of organic semiconductors is significantly reduced. System integration permits short signal paths, e.g. for the avoidance of beam spreading, scattering effects and background with optical detection.

The benefit however goes clearly beyond the pure addition or combination of the benefits attributable to each of the individual elements. In comparison to conventional centrifugal analyzers which use stationary detectors and sources of light, a system provided in accordance with the teaching of the present invention provides the following synergies:

- Possibility to decouple the rotationally controlled centrifugal actuation principle from the frequency and time window for detection which is also linked to the frequency of rotation when stationary components are used, as it is the case in state-of-the-art centrifugal analyzers.
- Increased sensitivity during the collection of characteristics of the fluid by the possibility of continuous collection of characteristics of the fluid.
- Simple processing of the continuously collected signal. This could be combined with, for example, on-substrate processing or pre-processing of the data through fabrication of suitable functional elements on the substrate.
- Where two or more cavities are provided it is possible to provide for simultaneous capture of a plurality of sample signals from the same substrate.
- Increased sensitivity during the collection of characteristics of the fluid by the direct radiative coupling of the generated signal into the fluid chamber and the direct measurement of a signal emitted. This is achievable by those arrangements where the functional element is intimately coupled to the substrate within which the fluid is provided.
- The recording of measurement by co-rotating detectors may require the transmission of the captured data from the rotatable substrate to a stationary receiver directly or via an intermediate data storage provided on the rotatable substrate. For this purpose functional elements can be integrated for the electronic processing, storage and transmission of data on the rotatable substrate. These components of the data processing can be made available for example from well-known microelectronic or opto-electronic functional elements as fabricated using organic semiconductors.

A device provided in accordance with the teaching of the invention may also be modified to provide data communication such as provided using vias, conductive paths or the like so as to allow for the transmission of data along the substrate. These conductive paths may also or alternatively be provided in the form of imprinted conductive strips on the central rotor, so as to allow the transmission of data from the substrate through sliding contacts to enable a transmission to a receiver provided in a stationary frame of reference.

It is also possible to fabricate a functional element in the form of, for example, a rotatable, directed emitting LED orientated so as to effect a signal transfer to a correspondingly positioned receiver(s) provided co-axially with the axis of rotation. In this way rotation of the substrate will not cause any interruption in the transfer of the optical signal between the functional element provided on the rotating substrate and its co-operating element provided in the stationary frame.

Figure 4:
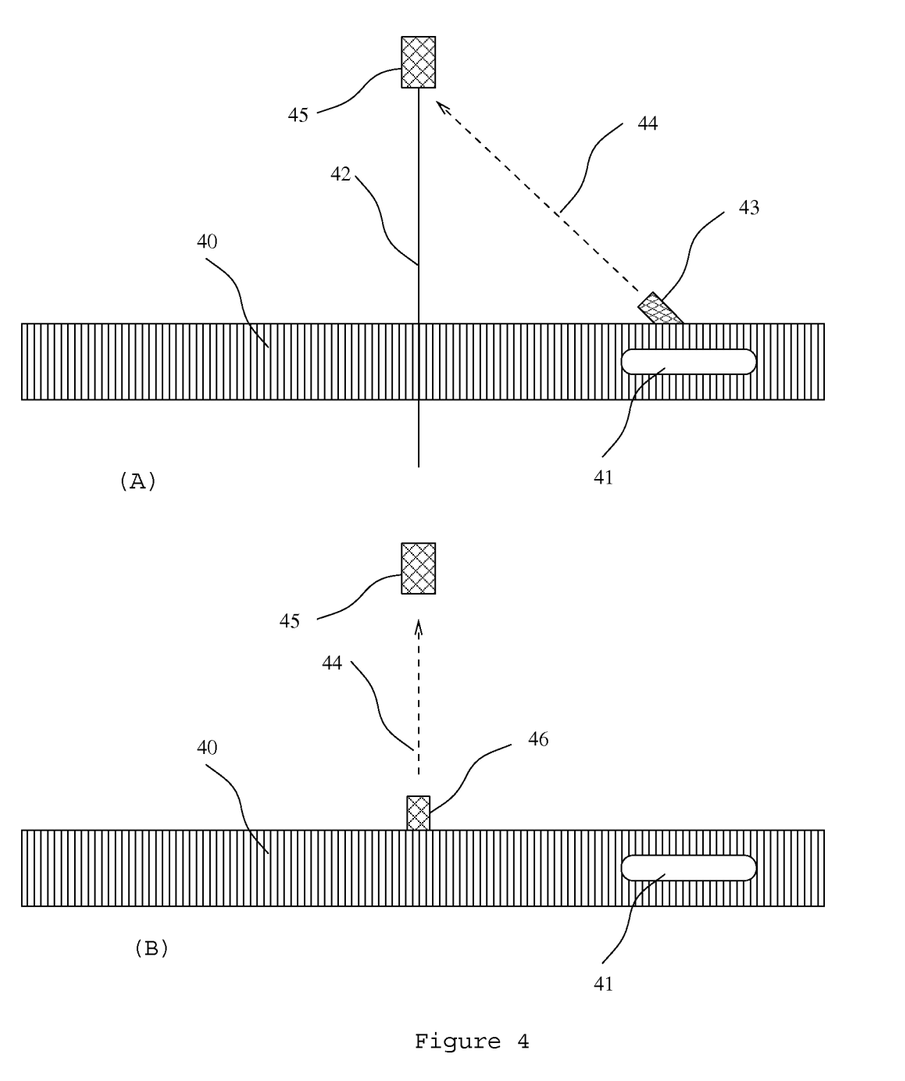
FIG. 4 shows two examples of how external communication may be provided.

Examples of such arrangements are shown in FIG. 4. In the schematic of FIG. 4A, a rotatable substrate (40) with a cavity (41) are rotatable about the axis provided by the axle (42). On the substrate (40) a signal source (43), provided for example in the form of an LED, is configured to send a signal (44) contactlessly to a detector (45) coaxially arranged on the axis of rotation (42). The nature of the detector will depend on the type of signal being transmitted but could for example be provided by a photodiode. In another configuration, shown in FIG. 4B, the transmitter (46) can be placed coaxially, so that the signal (44) arrives on a stationary course at the stationary detector (45). It will be appreciated that in the first arrangement the signal paths are not necessarily required on/in the substrate between the cavity (41) and the transmitter (43) whereas in the second arrangement, a conductive path will typically be required to enable a routing of information from the cavity (41) to the transmitter (46) located distally from the cavity. It will be appreciated that these schematics are representative of the transmission of information from the substrate to an external receiver. It will be appreciated that analogously information could be transmitted from the stationary reference frame to the substrate by exchanging the location of the transmitter and receivers respectively. In this way functional elements on the rotatable substrate could receive for example control signals from a stationary transmitter.

Captured data may be displayed on a peripheral device or an indicator like a screen or a printer which could be located remotely from the substrate. In an alternative arrangement the substrate could include for example an OLED display to provide for on-substrate displays.

Using stroboscopic principles it is possible to generate quasi standing picture so as to allow for identification of data during rotation of the substrate. Implementations of such principles could be achieved through for example use of flashlight exposure of information fields at an integral multiple of the turning frequency.

It will be appreciated that substrates provided in accordance with the teaching of the present invention could also be individually labeled and have additional data provided in for example human or machines readable format. Such data could for example be in the form of for example an alphanumeric value, graphics or bar code and could be used to differentiate between different substrates. An example of the type of technology that could be used to provide this data is the LightScribe™ technology provided by several optical disc drive (ODD) manufacturers.

In a further modification a device provided in accordance with the teaching of the present invention may provide a dual-function substrate. In addition to providing support for or defining one or more cavities therein, the substrate could be configured to provide for storage of the data generated through for example a substrate-based data track, as for instance in the format of recordable CD (Compact Disc) or DVDs (Digital Video Disc).

Potential applications of the invention described herein lie in fields, such as for example those already highlighted for conventional micro-fluid technologies [J. Ducrée and R. Zengerle, editor. Flow map—Microfluidics roadmap for the life sciences. Books on and GmbH, north first EDT, Germany, 2004. ISBN 3833407441.]. When applied as analytical tool, areas of particular interest include bioanalytics, biochemical and biomedical diagnostics. Examples for this are clinical chemistry, toxicology, serology, immune diagnostics, moleclear diagnostics inclusive PCR, protein crystallization and cell research.

Further applications lie in centrifugal microprocess engineering, for example with the production and treatment of multiphase systems and microspheres.

Due to the compactness, the user friendliness, portability and the costs in particular a device provided in accordance with the teaching of the present invention could be employed in a variety of environments including, for example, in the field of decentralized testing (e.g. field investigations in agriculture, flight safety) at the patient (e.g. point of care testing such as "patient self testing" or "bedside testing") or indeed in traditional environments such as doctor's offices, research laboratories and in medical large laboratories. It will be appreciated that what has been described herein are exemplary arrangements of a device having a rotatable substrates with one or more cavities to enable at least one of the admission, processing, or analysis of fluids, predominantly liquids and bio fluids such as blood, saliva and urine. The rotatable substrate is connected or associated with at least a further functional element which is desirably provided using organic semiconductors. By using organic semiconductors it is possible to fabricate film-based devices on the substrate that can withstand the pseudo forces that will be generated through the rotation of the substrate. The rotatable substrate can also include or be coupled to further functional elements fabricated from organic and/or non-organic materials. The functional elements may be fabricated off the substrate using conventional fabrication techniques and then assembled to the substrate in a hybrid integration process. The present invention also provides for the direct fabrication of the functional elements onto the substrate through use of processes compatible with the materials of the rotatable substrate. In another embodiment, the invention provides a device including a rotatable substrate with one or more cavities configured for receipt of a fluid therein, the substrate having at least one sensor element provided in communication with the one or more cavities, rotation of the substrate effecting a corresponding rotation of each of the one or more cavities and the at least one sensor element so as to enable a continuous monitoring of fluid within the one or more cavities during rotation of the substrate. By maintaining the sensor and the fluid within the same frame of reference during rotation of the fluid, it is possible to ensure that the frequency of monitoring is not limited to a once per rotation interaction between the sensor and the fluid within the cavity. Furthermore, as the sensor is intimately provided on the substrate with the fluid, the transmission path from the fluid to the cavity is well defined and of a short distance. Such a sensor device or element is desirably fabricated from an organic semiconductor.

The specific of the function provided by the one or more functional elements will include, for example, fluid processing, process control, power supply, energy transformation, electrical/electronic units and will serve electronic wiring, recording of temperature, production, modification and detection of electromagnetic radiation, for optical beam guidance, data processing, data storage, data communication or for the announcement of information for the user.

Examples of the application for specific functional elements fabricated from organic semiconductors are photodiodes for chemiluminescence detection, which together with a source of illumination (e.g. OLED, or polymer LED—pLED) could also be usefully employed in absorption or fluorescence measurements. Furthermore Peltier and thermal elements could be usefully fabricated for the recording of temperature or to effect an opening of thermally sensitive sacrificial layers provided within or on the substrate, energy management elements such as photovoltaic cells, for energy storage on the rotatable substrate, e.g. batteries, for the data processing, storage and communication (communication with stationary transmission/receipt unit, e.g. IR or optically). The results can be provided for the user either on stationary equipment, e.g. a PDA, or also over co-rotatable display or e.g. also over the LightScribe™

By incorporating active substrate-integrated heating and cooling sections it is possible to provide for controlled incubation temperatures or for example to effect controlled temperature ramps temporally and locally very exactly as with the PCR together with thermometer feedback. It will be further appreciated that using functional elements provided as part of the substrate that locally different temperature regimes may be implemented for example when parallel (simultaneous) processing or sequential going through different temperature zones on the same substrate is required.

The integration of the function required for the analysis tool onto the substrate that houses the cavity/cavities can lead to a reduction in the complexity of the peripheral equipment required to for example a conceptually simple, frequency-controlled rotary motor. By the employment of economical materials and their associated production technologies the rotatable substrate can be provided as a single use medical diagnostic tool. This can address any issues with regard to maintenance of traditional equipment and also addresses potential issues with regard to the comparatively short life span of the organic EL materials or components.

By the combining according to invention of rotatable substrates with functional elements on the basis of organic semiconductors, the advantages of hydrodynamics with the advantages of the use of components, specified above, which are based on organic semiconductors, steered via the rotating motion, can be synergetically united.

Therefore it will be appreciated that while the teaching of the present invention has been explained with reference to preferred implementations or embodiments that it is not intended to limit the application of the invention to that described herein as modifications can be made without departing from the spirit or scope of the present invention. Furthermore where constituents or components have been described with reference to any one Figure or example it will be understood that those integers or components could be exchanged with or used in combination with constituents or components described with reference to other Figures or components without departing from the teaching of the invention which is only to be limited insofar as is deemed necessary in the light of the appended claims which follow.

The words comprises/comprising when used in this specification are to specify the presence of stated features, constituents, steps or components but does not preclude the presence or addition of one or more other features, units, steps, components or groups thereof.

The invention claimed is:

1. A device including a rotatable substrate with one or more cavities configured for receipt of a fluid therein, the substrate comprising at least one functional element fabricated from an organic semiconductor, the at least one functional element being integrally provided with the substrate and providing at least one of an illumination source or a first detector to provide respectively at least one of optical excitation of the fluid within the one or more cavities or optical detection of an optical response of the fluid within the one or more cavities, rotation of the substrate about an axis of rotation effecting a corresponding rotation of each of the one or more cavities and the at least one functional element so as to allow for continuous illumination or detection of the fluid during the rotation of the substrate and wherein the substrate is configured to effect a transmission of data contactlessly to a second detector coaxially arranged on the axis of rotation, wherein the substrate comprises a conductive path to enable a routing of information from the one or more cavities to a transmitter located remotely from the one or more cavities, the transmitter providing for a transmission of the data to the second detector.

2. The device of claim 1 wherein the at least one functional element is configured to selectively induce effects within the fluid or determine the response of the fluid to an induced effect.

3. The device of claim 1 wherein the at least one functional element is configured to operably provide a source of electromagnetic radiation.

4. The device of claim 3 wherein the source of electromagnetic radiation provides for optical illumination of the fluid.

5. The device of claim 1 wherein the at least one functional element is responsive to optical properties of the fluid.

6. The device of claim 1 wherein the fluid is selected from at least one of a liquid, a gas, a suspension of particles or a mixture from several phases or substances.

7. The device of claim 1 configured such that during rotation of the substrate each of the fluid and the at least one functional element interact.

8. The device of claim 7 wherein the at least one of the one or more cavities defines a microstructure within the substrate.

9. The device of claim 1 wherein at least one of the one or more cavities are externally accessible to allow an introduction of the fluid into the cavities.

10. The device of claim 1 wherein at least one of the one or more cavities have dimensions less than a millimeter.

11. The device of claim 1 configured for collection of characteristics of the fluid within at least one of the one or more cavities.

12. The device of claim 11 wherein the characteristics collected include optical characteristics including at least one of: chemi-luminescence, bio-luminescence, fluorescence or optical density.

13. The device of claim 1 wherein the at least one functional element provides for a detection of electromagnetic radiation.

14. The device of claim 1 wherein the at least one functional element and fluid interact through generation of or detection of acoustic waves.

15. The device of claim 1 configured for detection of an impedance measurement.

16. The device of claim 1 element wherein the at least one functional element includes one or more electrodes.

17. The device of claim 1 wherein two or more cavities each having an associated at least one of the at least functional element to provide for two or more measurement outputs from the device.

18. The device of claim 17 wherein the two or more cavities are radially arranged about the substrate.

19. The device of claim 1 wherein the at least one functional element provides a detector configured for spatial discrimination of characteristics of the fluid.

20. The device of claim 1 wherein the at least one functional element is configured for inducing temperature changes within the fluid.

21. The device of claim 1 wherein the at least one functional element is configured for at least one of electronic processing, data storage, representation of data, display of data and/or transfer of data from the substrate.

22. The device of claim 1 including at least one of a photovoltaic cell and/or electrochemical cell.

23. The device of claim 1 wherein the at least one functional element is configured to provide at least one of a conduction, amplification, switching, sending and/or receipt of electrical signals.

24. The device of claim 1 wherein the at least one functional element is configured to provide at least one of a transmission, receipt, focusing, divergence, conduction, switching, division, filtering, diffraction or reflection of electromagnetic radiation.

25. The device of claim 1 wherein the at least one functional element is configured to provide at least one of spatial and/or phase identification of constituents within the fluid.

26. The device of claim 1 wherein the at least one functional element is configured to provide for the conversion of energy from one form to another.

27. The device of claim 1 wherein the at least one functional element is configured to provide for a storage or conduction of energy.

28. The device of claim 1 wherein the at least one functional element is configured to operably interact with elements in stationary components provided in an inertial or stationary frame of reference.

29. The device of claim 28 wherein the interaction is through one or more of magnetic or electrical fields.

30. The device of claim 28 wherein the interaction is through transmission of electromagnetic radiation.

31. The device of claim 1 wherein the at least one functional element is fabricated directly onto the substrate.

32. The device of claim 31 wherein the at least one functional element is formed on the substrate using one of liquid solution or vapor-phase processing.

33. The device of claim 1 wherein functional elements are fabricated remotely to the substrate and then coupled to the substrate to form a final assembled device.

34. The device of claim 1 wherein the at least one functional element is defined within a thin film provided on the substrate.

35. The device of claim 1 provided as a one-use device.

36. The device of claim 1 wherein the at least one functional element provides a synchronous light signal dependent on the rotation frequency of the substrate to generate a stationary or pseudo-stationary representation as viewed from the stationary reference frame.

37. A medical sensor including a device as claimed in claim 1.

38. An analysis tool including a device as claimed in claim 1.

39. A device including a rotatable substrate with one or more cavities configured for receipt of a fluid therein, the substrate comprising at least one functional element fabricated from an organic semiconductor, the at least one functional element being integrally provided with the substrate and providing at least one of an illumination source or a first detector to provide respectively at least one of optical excitation of the fluid within the one or more cavities or optical detection of an optical response of the fluid within the one or more cavities, rotation of the substrate about an axis of rotation effecting a corresponding rotation of each of the one or more cavities and the at least one functional element so as to allow for continuous illumination or detection of the fluid during the rotation of the substrate and wherein the substrate is configured to effect a transmission of data contactlessly to a second detector coaxially arranged on the axis of rotation, wherein the device comprises a transmitter provided separate to the rotatable substrate and configured to provide control signals to the rotatable substrate.

* * * * *